(12) United States Patent
Rathbun

(10) Patent No.: US 9,339,305 B2
(45) Date of Patent: May 17, 2016

(54) SNAP FIT ROD AND FASTENER SYSTEM

(75) Inventor: David Rathbun, Gap, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 251 days.

(21) Appl. No.: 13/235,949

(22) Filed: Sep. 19, 2011

(65) Prior Publication Data
US 2013/0072991 A1 Mar. 21, 2013

(51) Int. Cl.
*A61B 17/70* (2006.01)

(52) U.S. Cl.
CPC .......... *A61B 17/7041* (2013.01); *A61B 17/7037* (2013.01); *Y10T 29/49826* (2015.01); *Y10T 29/49863* (2015.01)

(58) Field of Classification Search
CPC ........... A61B 17/7035; A61B 17/7037; A61B 17/7041
USPC .......... 606/266–279, 305–308, 319, 328, 246
See application file for complete search history.

(56) References Cited

U.S. PATENT DOCUMENTS

| | | | |
|---|---|---|---|
| 2,651,766 A | 9/1953 | Runde | |
| 2,712,167 A | 7/1955 | Blanchard | |
| 4,707,051 A | 11/1987 | Hall | |
| 5,584,831 A | 12/1996 | McKay | |
| 5,609,593 A | 3/1997 | Errico et al. | |
| 5,647,873 A * | 7/1997 | Errico et al. | 606/264 |
| 5,741,252 A * | 4/1998 | Mazzio et al. | 606/54 |
| 5,752,954 A | 5/1998 | Mata et al. | |
| 5,810,814 A * | 9/1998 | Newson | 606/59 |
| 5,810,819 A | 9/1998 | Errico et al. | |
| 5,984,922 A | 11/1999 | McKay | |
| 5,997,539 A | 12/1999 | Errico et al. | |
| 6,022,348 A | 2/2000 | Spitzer | |
| 6,086,588 A * | 7/2000 | Ameil et al. | 606/266 |

(Continued)

FOREIGN PATENT DOCUMENTS

| | | |
|---|---|---|
| FR | 2856578 | 12/2004 |
| WO | 2005044117 | 5/2005 |

OTHER PUBLICATIONS

Synthes, Inc., Product Guide, "MATRIX Spine System. Snap-On Transconnectors.", (Nov. 2010), 8 pages.

(Continued)

*Primary Examiner* — Jan Christopher Merene
*Assistant Examiner* — Atiya Mahmud
(74) *Attorney, Agent, or Firm* — Meunier Carlin & Curfman LLC

(57) ABSTRACT

Implementations of the present disclosure provide a snap fit rod and fastener system including one or more fasteners for securing one or more rods to secure a spine or other anatomical structure. The fasteners include a fixation shaft, a clamp and a connector. The fixation shaft (for example a pedicle screw) is configured to frictionally engage a bone (vertebra) or other workpiece. The clamp has a pressure responsive portion that defines an opening configured to receive a rod. The connector is configured to connect the clamp to the fixation shaft and exert pressure on the clamp to modify the opening and secure the rod. A bias mechanism, such as a washer spring may be included to urge against the pressure responsive portion and which can be overcome by pressure on the rod for the "snap fit" effect. For additional adjustability, the clamp may be pivotally mounted on the fixation shaft.

21 Claims, 11 Drawing Sheets

(56) References Cited

U.S. PATENT DOCUMENTS

| | | | |
|---|---|---|---|
| 6,342,054 B1 | 1/2002 | Mata | |
| 6,371,957 B1* | 4/2002 | Amrein et al. | 606/272 |
| 6,682,532 B2* | 1/2004 | Johnson et al. | 606/264 |
| 7,166,109 B2 | 1/2007 | Biedermann et al. | |
| 7,569,070 B2 | 8/2009 | Suzuki et al. | |
| 7,695,498 B2 | 4/2010 | Ritland | |
| 7,806,623 B2 | 10/2010 | Thomke et al. | |
| 8,506,598 B1* | 8/2013 | Tohmeh | 606/264 |
| 2006/0079899 A1 | 4/2006 | Ritland | |
| 2006/0149231 A1 | 7/2006 | Bray | |
| 2006/0247629 A1* | 11/2006 | Maughan et al. | 606/61 |
| 2007/0161987 A1 | 7/2007 | Capote et al. | |
| 2007/0233066 A1* | 10/2007 | Rezach | 606/61 |
| 2008/0021467 A1* | 1/2008 | Schumacher et al. | 606/61 |
| 2008/0312696 A1* | 12/2008 | Butters et al. | 606/264 |
| 2009/0099604 A1* | 4/2009 | Cho et al. | 606/250 |
| 2009/0287253 A1 | 11/2009 | Felix et al. | |
| 2010/0049253 A1* | 2/2010 | Miller | 606/264 |
| 2010/0168796 A1 | 7/2010 | Eliasen et al. | |
| 2010/0204733 A1 | 8/2010 | Rathbun et al. | |
| 2010/0211100 A1 | 8/2010 | Mack | |
| 2010/0268279 A1 | 10/2010 | Gabelberger et al. | |

OTHER PUBLICATIONS

Synthes, Inc., Product Guide, "USS Variable Axis Screw (VAS). Removal instructions.", (Feb. 2011), 8 pages.

Notification of Transmittal of the International Search Report and the Written Opinion, dated Nov. 22, 2012, in International Application No. PCT/US2012/056005.

* cited by examiner

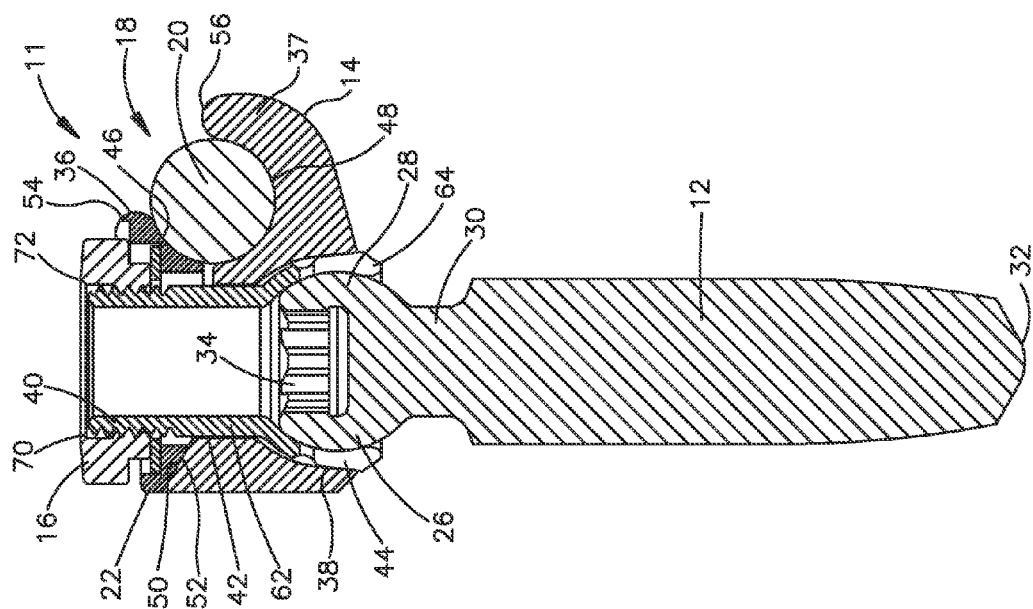
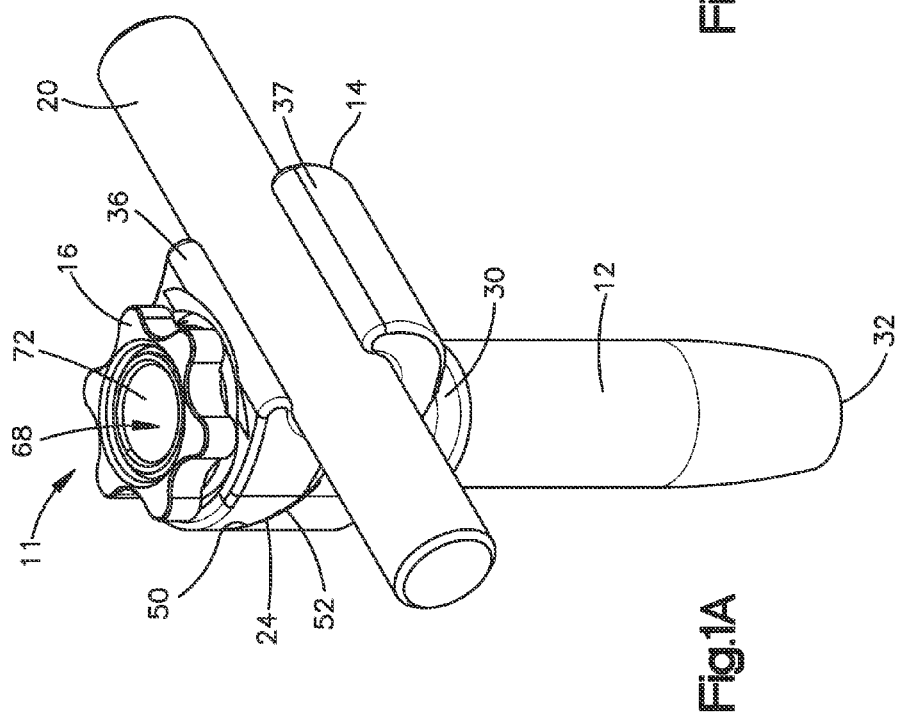
Fig.1B
Fig.1A

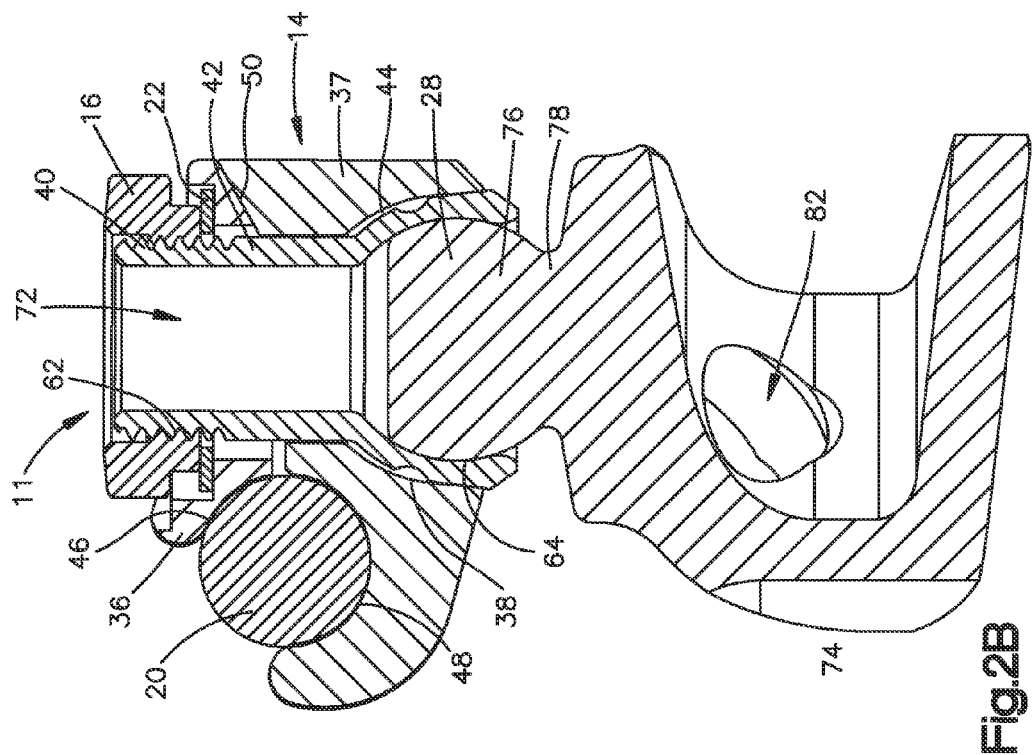
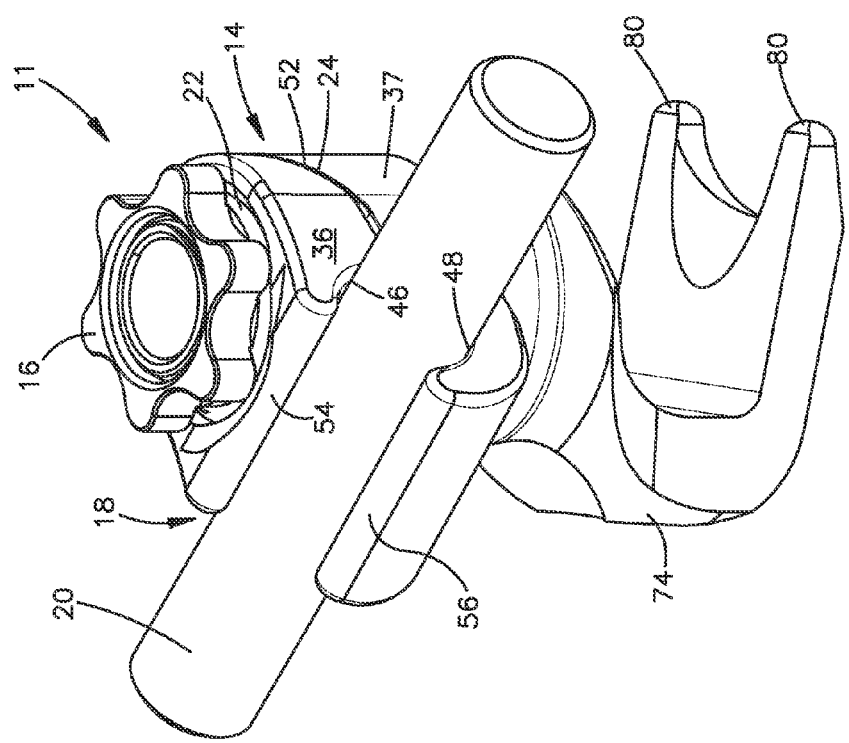

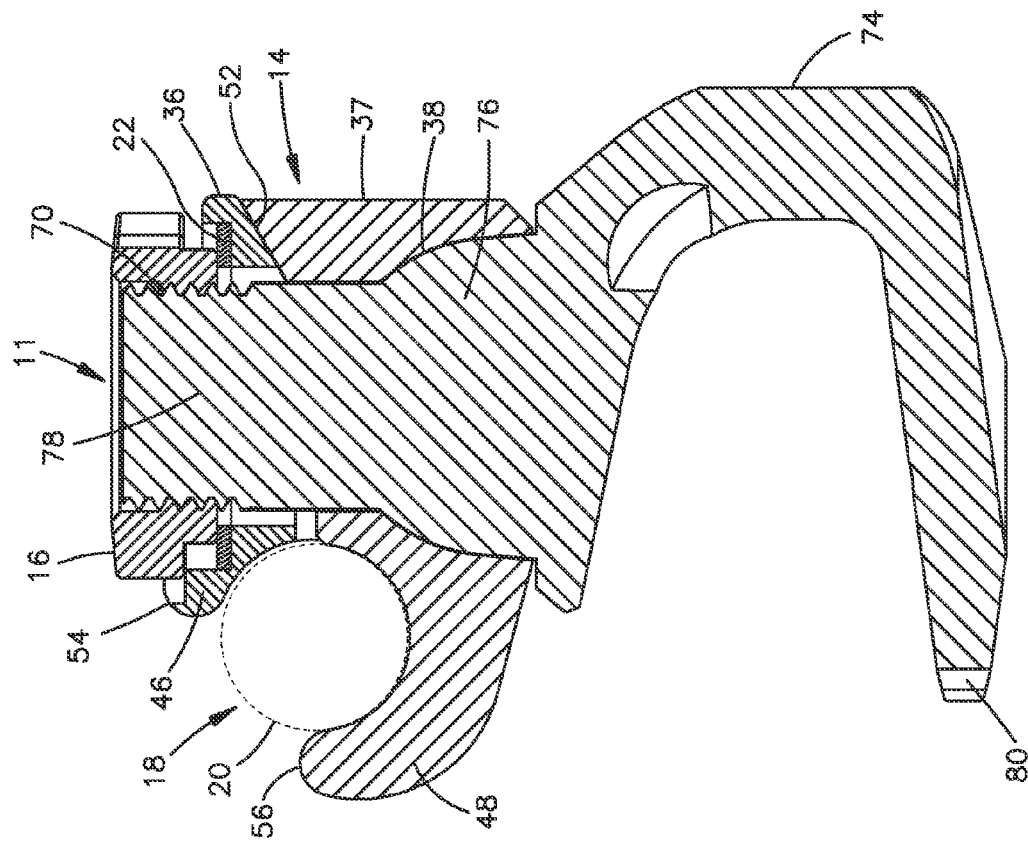
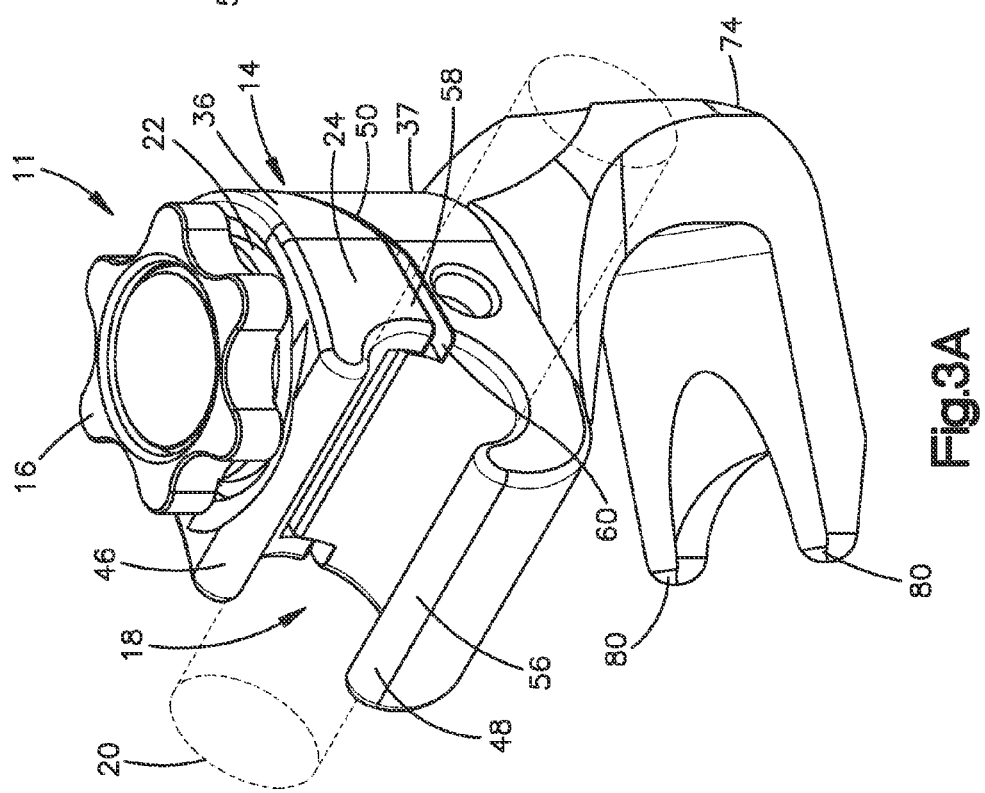

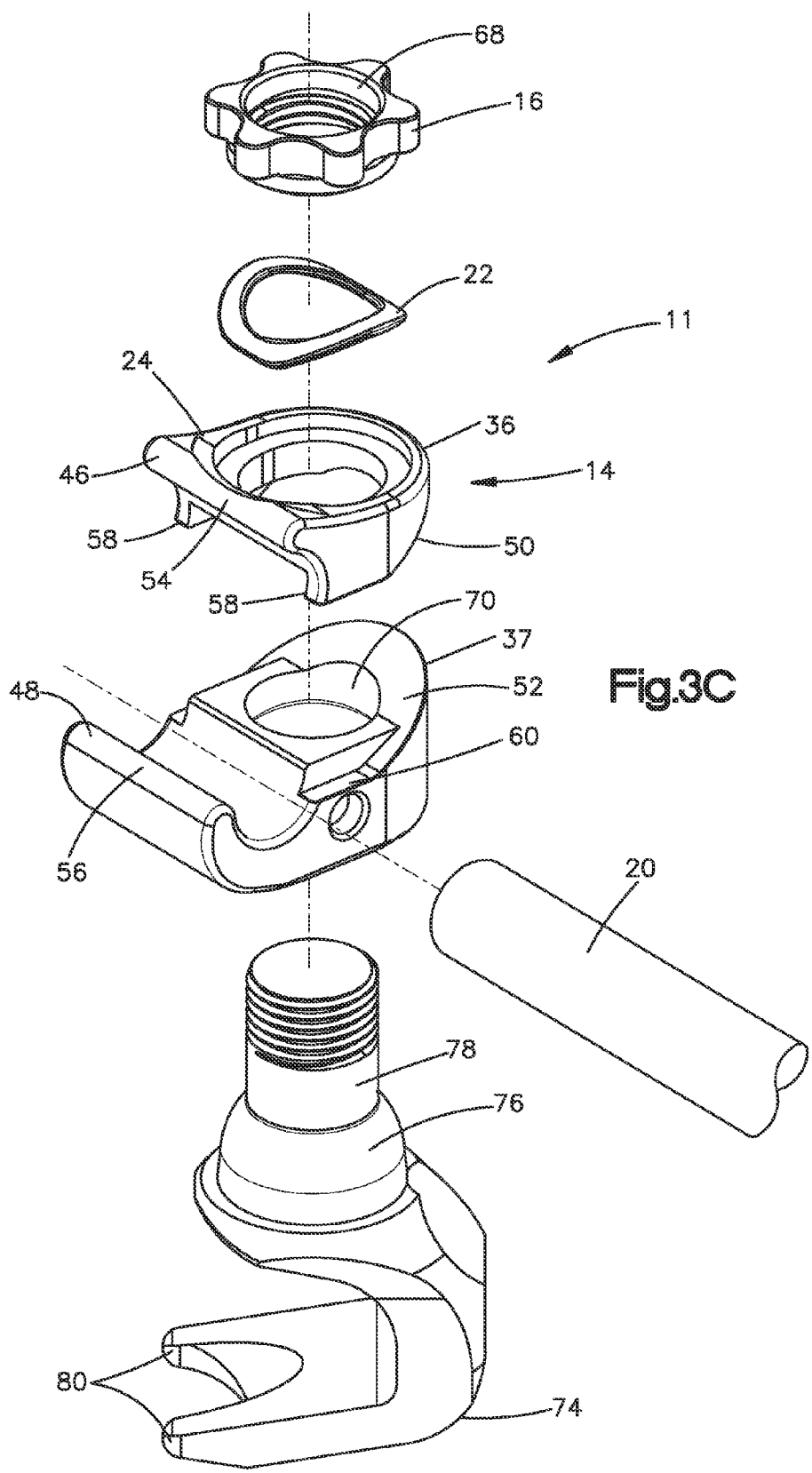

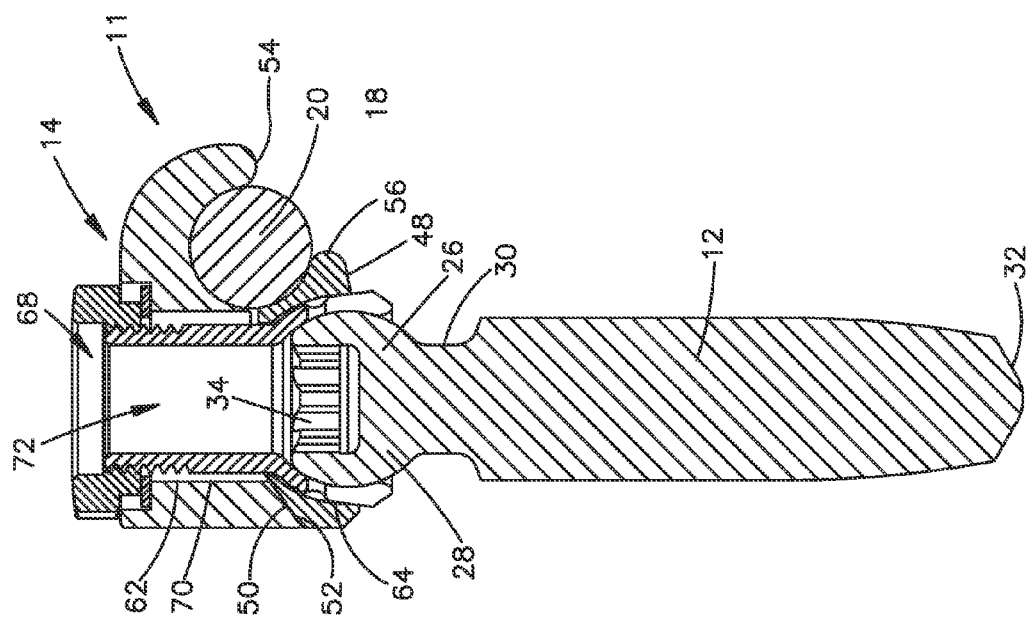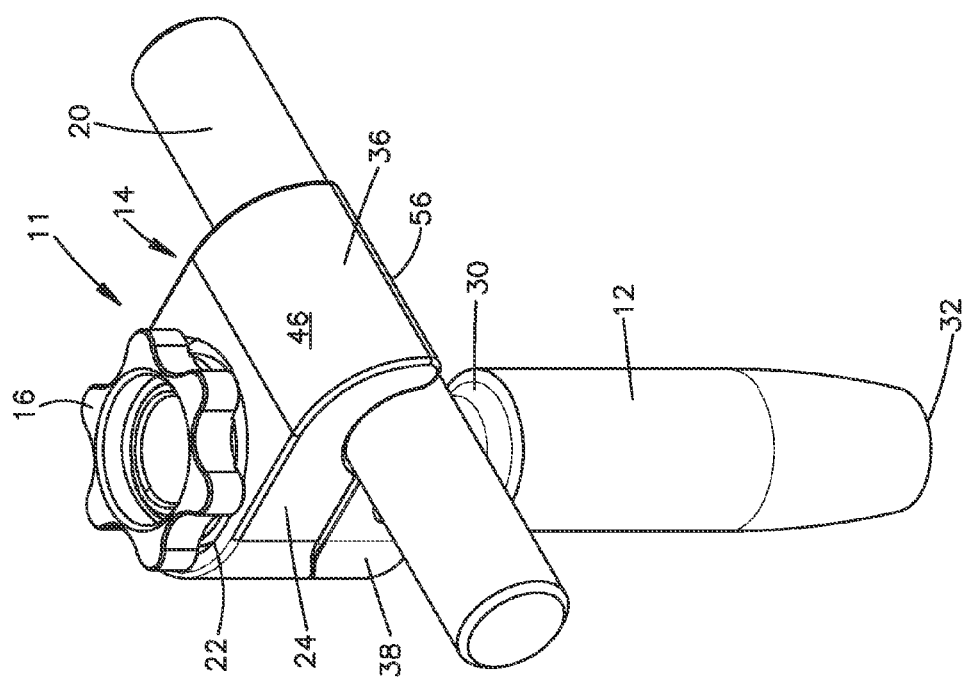

SNAP FIT ROD AND FASTENER SYSTEM

BACKGROUND

Pedicle screws coupled with longitudinal rods are used to correct or stabilize anatomical lumbar and thoracic spinal deformity, degenerative, spondylolisthesis, trauma, tumor, stenosis or pseudarthrosis conditions of skeletally mature patients.

Existing rod systems include a pedicle screw with a clamp that has a pair of arms mounted to a proximal end of the pedicle screw. A rod is slid into an opening in the clamp between the two arms and then a fastener, such as nut, is attached to close off the opening between the arms of the clamp. Although providing a secure attachment, this is a slow, labor-intensive process for assembling rods and pedicle screws into final orthopedic fixation. Also, post-assembly adjustments are difficult to make as each attachment is relatively rigid upon securing the fastener.

SUMMARY

Implementations of the present disclosure overcome the problems of the prior art by providing a fastener for engaging a workpiece opening. The fastener includes a fixation shaft, a clamp and a connector. The fixation shaft is configured to frictionally engage the workpiece opening. Included in the clamp is a pressure-responsive portion. The clamp at least partially defines an opening wherein the pressure-responsive portion is configured to modify the opening in response to pressure. The connector is configured to connect the clamp to the fixation shaft and exert pressure on the pressure-responsive portion of the clamp so as to modify the opening. The clamp is configured to pivotally engage a proximal end of the fixation shaft.

The pressure responsive portion may be configured to decrease the size of the opening in response to the application of pressure. Pressure may also cause locking engagement of the clamp with the proximal end of the shaft.

A proximal end of the fixation shaft may include an at least partially spherical head and the clamp may include a semi-spherical opening configured to receive the spherical head. Included in the clamp may be a collet that defines the semi-spherical opening. The collet may be configured to compress the spherical head within the semi-spherical opening for locking engagement. Also, the collet may include a skirt that defines the semi-spherical opening and a shaft extending from the skirt. The shaft may be configured to extend into an opening defined in a body of the clamp.

The connector can be configured to connect to the shaft of the collet and, upon tightening, compress the body of the clamp therebetween. Compression of the body of the clamp in turn deforms the skirt to lock the collet onto the spherical head. The connector may be a threaded nut configured to engage a plurality of threads on the shaft of the collet. The shaft of the collet may define an axial opening and be configured for alignment with an axial opening of the nut when engaged thereto.

The skirt may define one or more radial relief cuts configured to facilitate deformation of the skirt about the spherical head. A bias mechanism, such as a spring washer, may be configured for placement between the threaded nut and the body of the clamp.

Included in the clamp may be an upper body and a main body that together define the clamp opening. The upper body may include as sloped surface and the main body a sloped surface, wherein the sloped surfaces define the pressure-responsive portion. Also, the upper body may include an arc member and the main body an arc member. These arc members are configured to define an opening of the clamp, such as a cylindrical opening.

Advantageously, the sloped surfaces may be configured to result in both lateral and vertical movement of the upper body portion with respect to the main body portion upon exertion of pressure by the connector. This lateral movement can shorten a distance between the free ends of the arc members.

A spring may extend between the upper body and the connector wherein the spring is configured for deformation by external pressure urging the free ends of the arc members apart. These free ends may be shaped to act as cam members. And, the spring may be configured to assume a fully deformed condition upon tightening of the connector which can lock relative movement of the body portions.

The skirt may be configured to allow plus or minus 30 degrees of tilt of the clamp with respect to a plane orthogonal to an axis of the fixation shaft. Also, the arc member of the upper body may be shorter than the arc member of the main body so as to define an upwardly directed slot accessing the opening of the clamp. The reverse may also be employed to define a downwardly directed slot.

A method of engaging a workpiece and attaching a rod to a fastener includes fixing a shaft to the workpiece by frictionally engaging the shaft into an opening of the workpiece. A clamp may be pivoted with respect to the shaft and the rod placed within an opening defined by a clamp coupled to the shaft. The method also includes modifying the opening to lock the clamp onto the rod by exerting pressure on the clamp with a connector.

Modifying the opening may include decreasing a size of the opening.

Pivoting the clamp may include pivoting the clamp at least plus or minus 30 degrees of tilt of the clamp with respect to a plane orthogonal to an axis of the fixation shaft.

Placing the rod may include urging apart two body portions of the clamp and slipping the rod therebetween. Decreasing the size of the opening may include urging together the two body portions of the clamp after slipping the rod therebetween.

Exertion of pressure on the clamp may simultaneously lock the clamp onto the rod and lock the clamp with respect to the shaft to stop further pivoting of the clamp. Fixing the shaft can include engaging a proximal end of the shaft with a driver by extending the driver through an axial opening in the connector and an axial opening in the clamp.

Exerting pressure may also include engaging the connector with a driver after engaging the proximal end of the shaft and placing the rod within the opening.

The clamp itself may be separately (step-wise) coupled to a proximal end of the shaft, such as by inserting a spherical head of the shaft within a semi-spherical opening of the clamp.

Also, the method may include extending a shaft of a collet into an axial opening defined in a body of the clamp and attaching the connector to the shaft of the collet and compressing the body of the clamp therebetween. Compression of the body may deform the skirt to lock onto the spherical head and may compress a spring between the connector and a skirt of the collet.

Attaching the connector may include screwing threads of the connector onto threads of the shaft of the collet.

Modifying the opening may include sliding a sloped surface of an upper body portion along a sloped surface of a main body portion of the clamp. Also, it may include advancing an arc member of the upper body portion closer to an arc member of the main body portion. For example, the arc members may be advanced laterally and vertically with respect to one another. In addition, the arc members may be urged together with a spring. Conversely, placing the rod may include urging free ends of the arc members apart by overcoming a bias of the spring. After the rod is placed, the spring bias may urge the arc members together again in abutting engagement with the rod. Exerting pressure on the clamp may include overcoming the bias of the spring.

These and other features and advantages of the implementations of the present disclosure will become more readily apparent to those skilled in the art upon consideration of the following detailed description and accompanying drawings, which describe both the preferred and alternative implementations of the present disclosure.

BRIEF DESCRIPTION OF THE DRAWINGS

FIG. 1A is a perspective view of a snap-fit fastener including a clamp for a rod;

FIG. 1B is a cross-sectional view of the fastener of FIG. 1A;

FIG. 2A is a perspective view of another fastener including a clamp mounted on a hook;

FIG. 2B is a cross-sectional view of the fastener of FIG. 2A;

FIG. 3A is a perspective view of a fastener with a hook and a downward clamp opening orientation;

FIG. 3B is a cross-sectional view of FIG. 3A;

FIG. 3C is an exploded view of the fastener of FIG. 3A;

FIG. 4A is a perspective view of a snap-fit fastener with a downward clamp opening orientation;

FIG. 4B is a cross-sectional view of FIG. 4A;

DETAILED DESCRIPTION

Implementations of the present disclosure now will be described more fully hereinafter. Indeed, these implementations can be embodied in many different forms and should not be construed as limited to the implementations set forth herein; rather, these implementations are provided so that this disclosure will satisfy applicable legal requirements. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms.

Figure 4C:
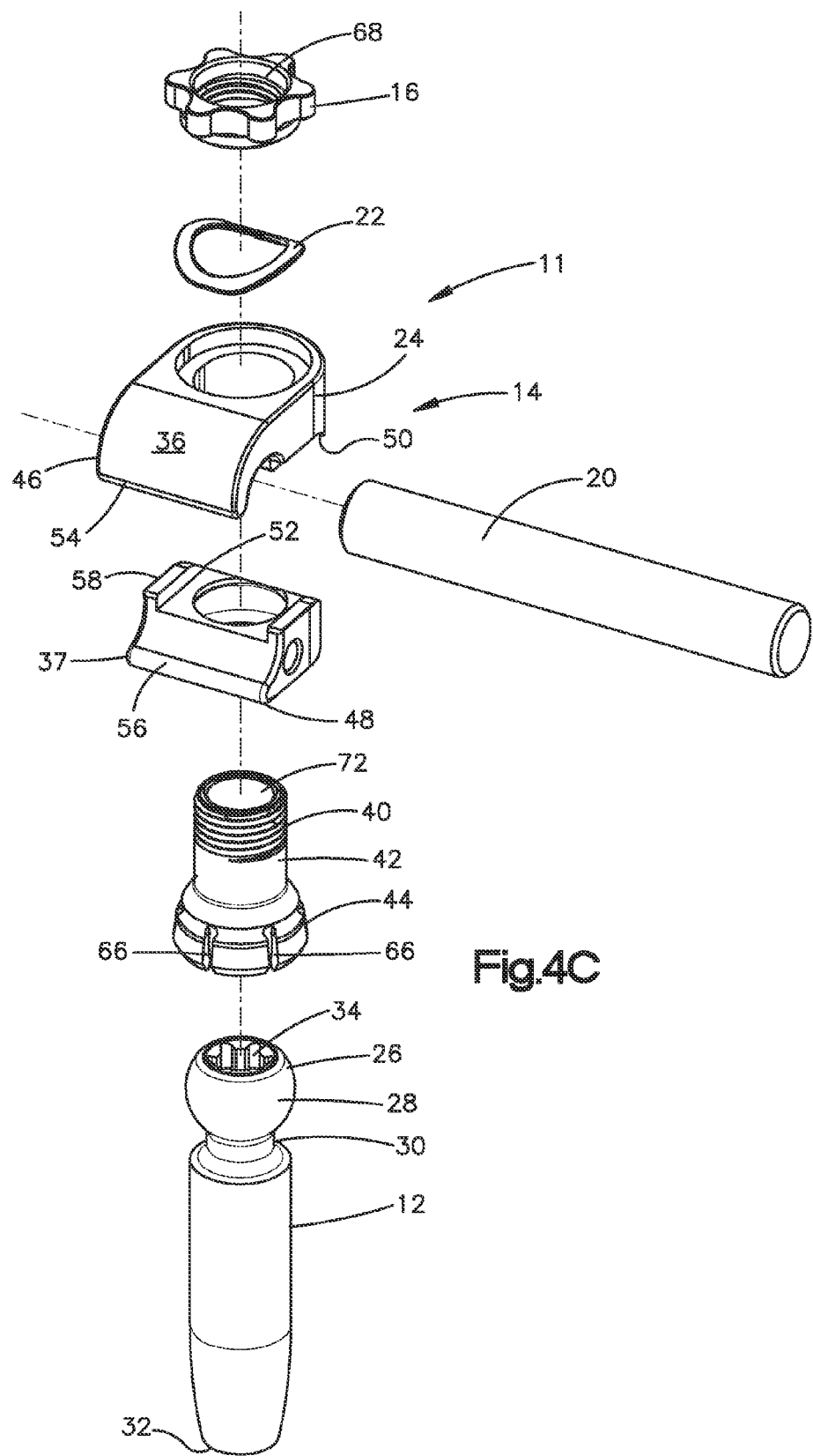
FIG. 4C is an exploded view of FIG. 4A.
Figure 5:
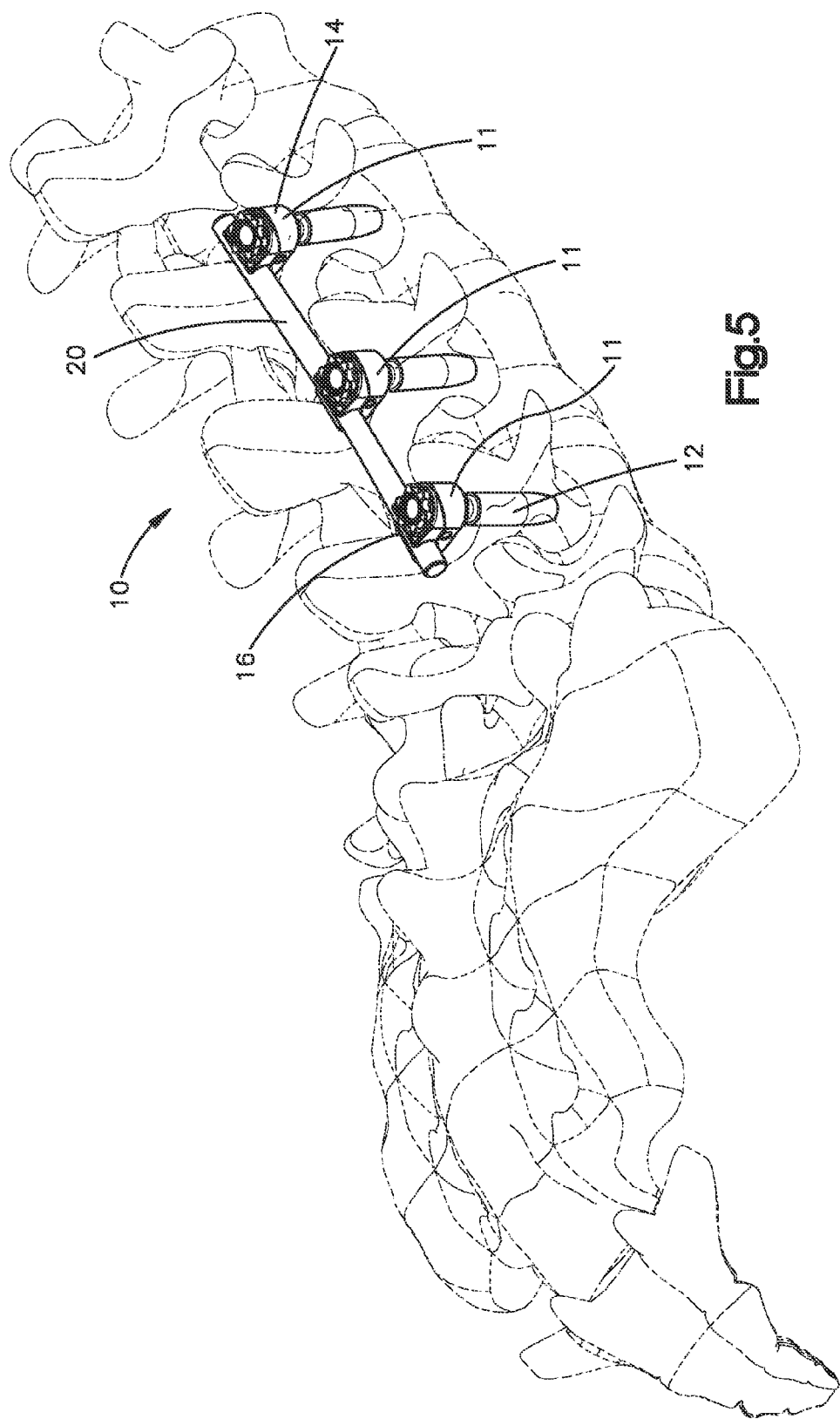
FIG. 5 is a perspective view of a rod and snap-fit fastener system.

A snap fit rod and fastener system 10 is shown in the accompanying FIGS. 1-7. The system 10 includes one or more fasteners 11 for securing one or more rods 20 to secure a spine or other anatomical structure, as shown in FIG. 5.

The fasteners 11 include a fixation shaft 12, a clamp 14 and a connector 16. The fixation shaft 12 (for example a pedicle screw) is configured to frictionally engage a bone (vertebra) or other work piece. The clamp 14 has a pressure responsive portion 24 that defines an opening 18 configured to receive one of the rods 20, as show in FIG. 1A. The connector 16 is configured to connect the clamp 14 to the fixation shaft 12 and to (optionally) simultaneously exert pressure on the clamp 14 to modify the opening and secure the rod.

Figure 1C:
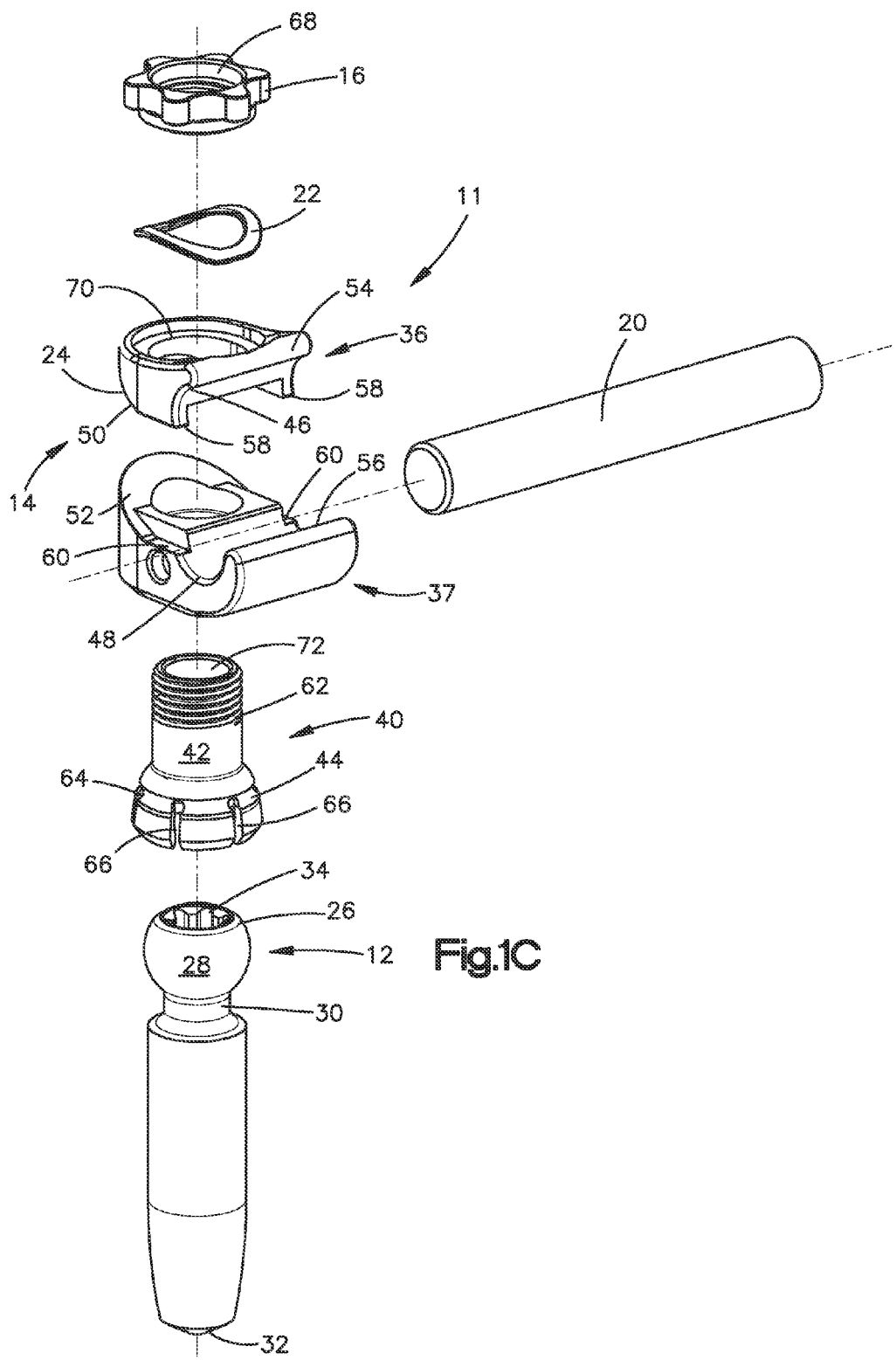
FIG. 1C is an exploded view of the fastener of FIG. 1A.

A bias mechanism, such as a washer spring 22 as shown in FIG. 1C, may be included to urge against the pressure responsive portion 24. The washer spring 22 can be overcome by pressure on the rod 20 for the "snap fit" effect. For additional adjustability, the clamp 14 may be pivotally mounted on the fixation shaft 12. Spring bias can also originated in the bending flexibility and/or compressibility of the components, such as the clamp 14 itself.

Advantageously, the system 10 may be adjusted and temporarily configured with the snap fit effect with some play in the system for fine adjustments, or larger reorientations based on the pivot attachment of the clamp, before finally being secured. Also, the fasteners 11 may be attached to the bone or other work piece in an assembled, but not tightened, condition so that time consuming steps for later attachment of the connector 16 are avoided.

The fasteners 11 may be pedicle screws, but also may include regular screws or threaded rods or other devices capable of frictionally engaging bone or some other work piece in a surgical setting. As shown in FIG. 1B, the fastener 11 includes a proximal end 26 having a semi-spherical head 28, a neck 30 and a distal end 32. The distal end 32 is threaded for engagement of bone either in an existing opening or by forming its own opening upon attachment. The distal end 32 could also frictionally engage through expansion or the friction associated with nail or pin driven into the bone. The distal end 32 of the fastener 11 shown in FIG. 1A has a taper to it to facilitate insertion and attachment into the bone.

The neck 30 is a narrowing of the diameter of the fastener 11 and a gradual transition to the base of the semi-spherical head 28 at the proximal end 26. The semi-spherical head 28 attaches at its distal bottom to the neck 30 and at its top defines an internal driver opening 34 with a star shape. Other shapes for the driver opening 34 could be employed although the star shape has the advantage of being particularly secure against stripping or slipping. The pedicle screw may be a dual core and double lead bone thread with the aforementioned spherical head 28. Although other shapes could be used for the head of the fasteners 11, the spherical head 28 has particular advantages for pivotal adjustment.

The clamp 14 may include a pair of jaws or body portions, including an upper jaw 36 and a main (or lower) jaw 37, as shown in FIG. 1C. The upper and main jaws 36, 37 each include an arc member 46, 48, respectively, that when assembled define the clamp opening 18. Each of the arc members, for example, may have an internal surface that is part of a cylindrical shape for receiving a cylindrical rod 20, as shown in FIG. 1B. The jaws 36, 37 may also have other shapes, such as an L-shape and define different clamp opening 18 shapes, such as a rectangular, oval or square shape, for receiving a rod 20 have a rectangular cross-section.

Also, the arc member 46 of the upper jaw 16 includes a free end 54 and the arc member 58 of the main jaw 37 includes a free end 56. The free ends 54, 56 cooperate to define a slot for access to the clamp opening 18, as shown in FIG. 1A. The free ends 54, 56 may also include rounded cam surfaces that facilitate smooth, guided insertion of the rod 20 during the snap fit process, as will be described in more detail below.

The upper jaw 36 and main jaw 37 also define adjacent interacting surfaces and an axial opening 70, including surfaces perpendicular to the axis of the axial opening 70 and sloped surfaces at an angle to the axis of the opening 70. For example, the upper jaw 36 includes a sloped surface 50 and the main jaw 37 includes a sloped surface 52, as shown in FIGS. 1B and 1C. The sloped surfaces 50, 52 are positioned at a rear end of each of the jaws 36, 37 opposite the arc members 46 and 48. In the middle of the jaws 36, 37 are flat surfaces that are perpendicular to the axis of the opening 70, these surfaces extending more adjacent and around the axial opening 70.

Additionally, the upper jaw 36 may include a pair of flanges 58 configured to extend down into corresponding slots 60 defined on the main jaw 37, as shown in FIG. 1C. Engagement of flanges 58 and slots 60 (which could be switched or alternated (one on each of the jaws) helps to stabilize and align the jaws 36, 37. Between the flanges 58 and the slots 60 are perpendicular (to the axial opening 70) surfaces that are generally parallel and/or abutting when assembled, as shown in FIG. 1B. Also, the sloped surfaces 50, 52 slide along each other during the snap-fit process so as to allow relative movement of the free ends 54, 56 of the jaws against a bias, such as the washer spring 22, as will be described in more detail below.

The upper jaw 36 may also include a recess for the spring washer 22.

The axial opening 70 shown in FIG. 1B extends through both of the jaws 36, 37 and has a cylindrical top portion 62 and a semi-spherical bottom portion 64. Also included in the clamp is a collet 40 which itself includes the shaft 42 and skirt 44. The shaft 42 of the collet 40 is threaded and configured to extend through the top portion 62 of the axial opening 70 of the clamp defined partially in each of the jaws 36, 37. The skirt 44 has a semi-spherical configuration and is configured to extend within and along (or close by) the walls of the main jaw 37 defining the semispherical bottom portion 64. Enough of the shaft 42 of the collet 40 extends out of the proximal end of the upper jaw 36 to pass the washer spring 22 and connect via threads to the connector 16.

The drive nut or connector 16 has a star (hexalubular) shape and a central opening 68 with internal threads that allow it to engage the threads on the shaft 42 of the collet 40. Also, the central opening 68 of the connector 16 allows access to an axial opening 72 defined by the shaft of the collet 40 so that a driver can access the driver opening 34 on the proximal end of the fixation shaft 26.

The skirt 44 of the collet 40 has radial slots 66 that separate the skirt into flexible finger portions. The finger portions have a circumferential notch (or notches) for reduced thickness at their proximal ends to further promote flexibility. Advantageously, the flexibility promotes locking of the clamp 14 about the spherical head 28 of the pedicle screw 12. Tightening of the connector 16 onto the shaft 42 of the collet with the spherical head within the skirt 44 deforms its fingers inwards into a tight fit about the spherical head by pulling the skirt into the semi-spherical clamp opening 38.

Tightening of the connector 16 also compresses the washer spring 22 and two jaws 36, 37 together in a manner that causes the sloped surfaces to shift the arc member 46 of the upper jaw 36 axially and laterally toward the arc member 48 of the main jaw 37 to reduce the size of the clamp opening 18 and the slot between the free ends 54, 56 of the arc members. Thus, at the same time the skirt 44 is tightened in its connection to the spherical head of the fixation shaft 12, the jaws 36, 37 are articulating to lock onto the rod 20.

The washer spring 22 may be substituted or combined with other spring biases (or done away with entirely) depending upon the amount of tactile force desired for the snap fit. The other biasing or spring mechanisms that may be used include biasing mechanisms such as the bending stiffness of the jaws 36, 37 themselves, a cantilever, a coil spring, etc. The spring washer 22 may be constructed of a nitinol material for a large range of elasticity. It provides an axial spreading force that pushes the upper jaw 36 down and lateral with respect to the main jaw 37.

Referring now to FIG. 5, assembly of the system 10 includes placement of a plurality of fasteners 11 by driving the spherical head 28 of the fixation shaft 12 (with the clamp 14 and connector 16 loosely attached) through the opening in the connector 16 and the axial opening 72 of the clamp 14. Once several of the fasteners 11 are placed in a desired arrangement, the clamps 14 can be oriented to rotate or pivot on the spherical head 28 of the fixation shaft 12 via the loose fit of the skirt 44 of the collet 40 on the spherical head 28. The skirt 44 is shaped and sized to allow a relatively wide range of pivoting motion, such as plus or minus 30 degrees of tilt of the clamp 14 with respect to a plane orthogonal to an axis of the fixation shaft 12. These enhanced angulations and offset head positioning advantageously reduce time spent bending the rods 20 because the clamp 14 moves to meet the rod instead of vice-versa.

Regardless, once the fasteners 11 are in place, the rod 20 can be routed and snapped in through the slot between the free ends 54, 56 of the arc members 46, 48. The snap fit occurs by the pressure of the rounded surface of the rod 20 pushing against the rounded, cam surface of the free ends 54, 56 until the bias of the washer spring 22, and other applicable biases of the flexibility of the clamp 14 components or the collet skirt 44, are overcome. This pressure drives the free ends 54, 56 apart and the upper jaw 36 slides laterally and away, along the sloped surfaces 50, 52, from the main jaw 37.

At this point, the rod 20 seats into the clamp opening 18 and the bias of the washer spring 22 reverses the direction of the jaws bringing their free ends 54, 56 together. This snap-fit hold is firm enough to allow the other rod-to-fastener 11 attachments, and accompanying bending and/or reorientation of the components of the assembly 10. Once all components are relatively positioned, the healthcare personnel can proceed amongst the fasteners 11 begin securing each connector 16. As each connector 16 is tightened to the end of the collet shaft 42, the washer spring 22 is again overcome and the jaws 36, 37 are locked in their relative position against further movement. The slot between the free ends 54, 56 becomes too small for the rod 20 to pry free.

Advantageously, the snap-in rod feature does not require a second component (locking cap) that has to be inserted after the rod 20 has been reduced to the pedicle screw 12 which can save time and money in the operating room and reduce risk to patients. The snap-in feature also enhances confidence through visual indication that the rod 20 has been correctly placed in the patient because the connector or drive nut 16 is on a different axis from the rod 20. Also, the reduction instruments may have reduced cannulations to accommodate the connector 16.

Although shown as having all the fasteners 11 positioned on one side of the rod 20 in FIG. 5, the system 10 can be situated with the fasteners on either or alternate sides of the rod because of the pivot ability of the clamp 14 with respect to the fixation shaft 12. The rod 20 may also be bent or curved at smoother angles to reduce strain due to the angular adjustability and selective placement.

Options for the system 10 include a release for the skirt 44 or clamp 14 by way of loosening the connector 16 so that the clamp 14 may pop on-and-off the pedicle bone screw head. Also, head design could be varied (e.g., tilting at the neck 30) to allow different standoff heights—i.e., the height of the rod 20 above or away from the bone. The clamps 14 could also be varied to accept different diameter rods 20, such as by altering the curvature and length of the arc members 46, 48.

Figure 6:
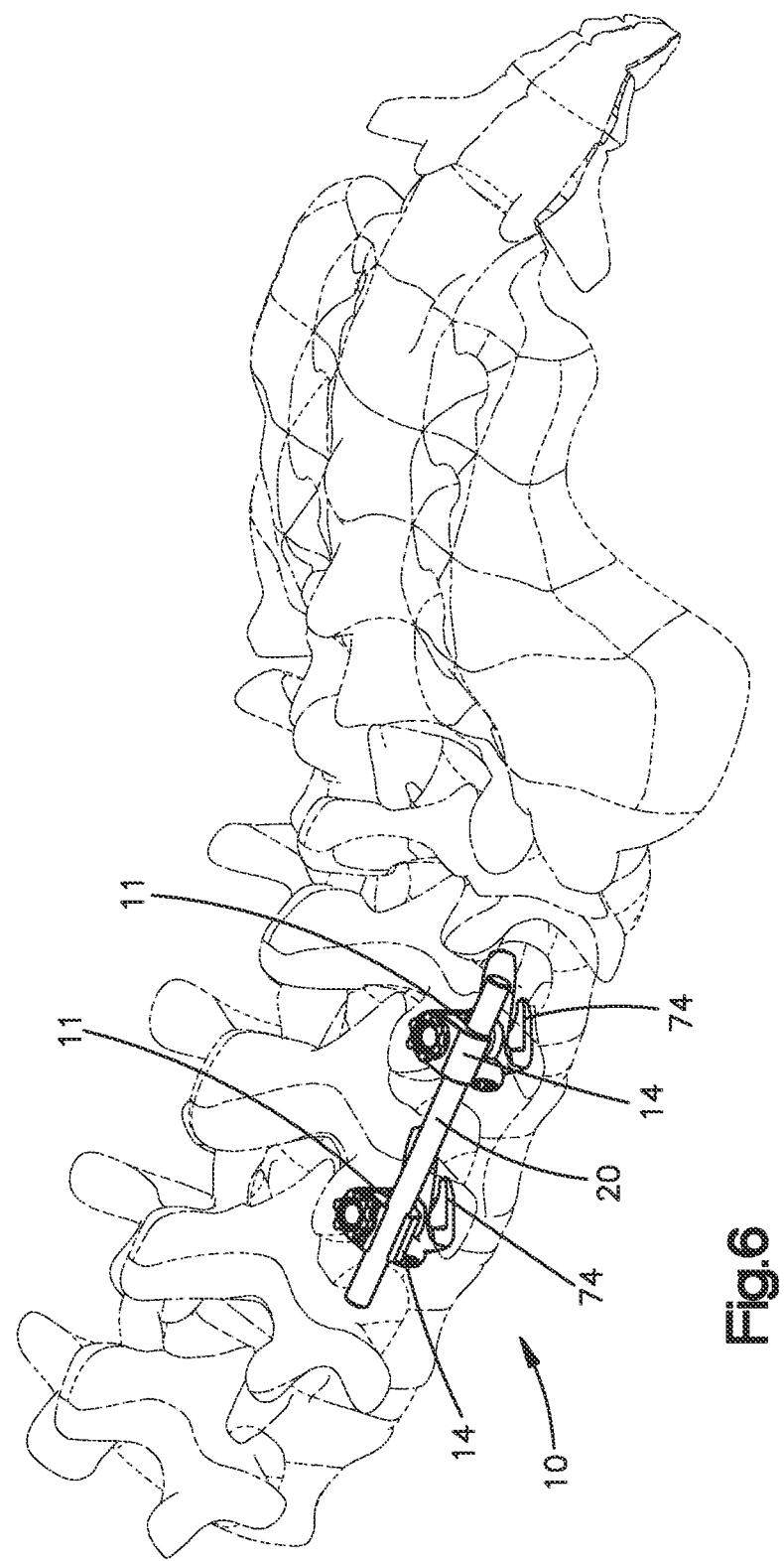
FIG. 6 is a perspective view of another rod and snap-fit fastener system.

Rod acceptance angles could also be varied, such as, for instance, changing the relative length and positioning of the arc members 46, 48. For example, as shown in FIGS. 4A-C, the ends 54, 56 of the arc members 46, 48 are oriented downward or proximal toward the bone of the spine. FIG. 6 shows upward and downward orientation of the clamp opening. In this configuration, the arc member 48 of the main jaw 37 is smaller than the arc member 46 of the upper jaw 36.

Figure 7:
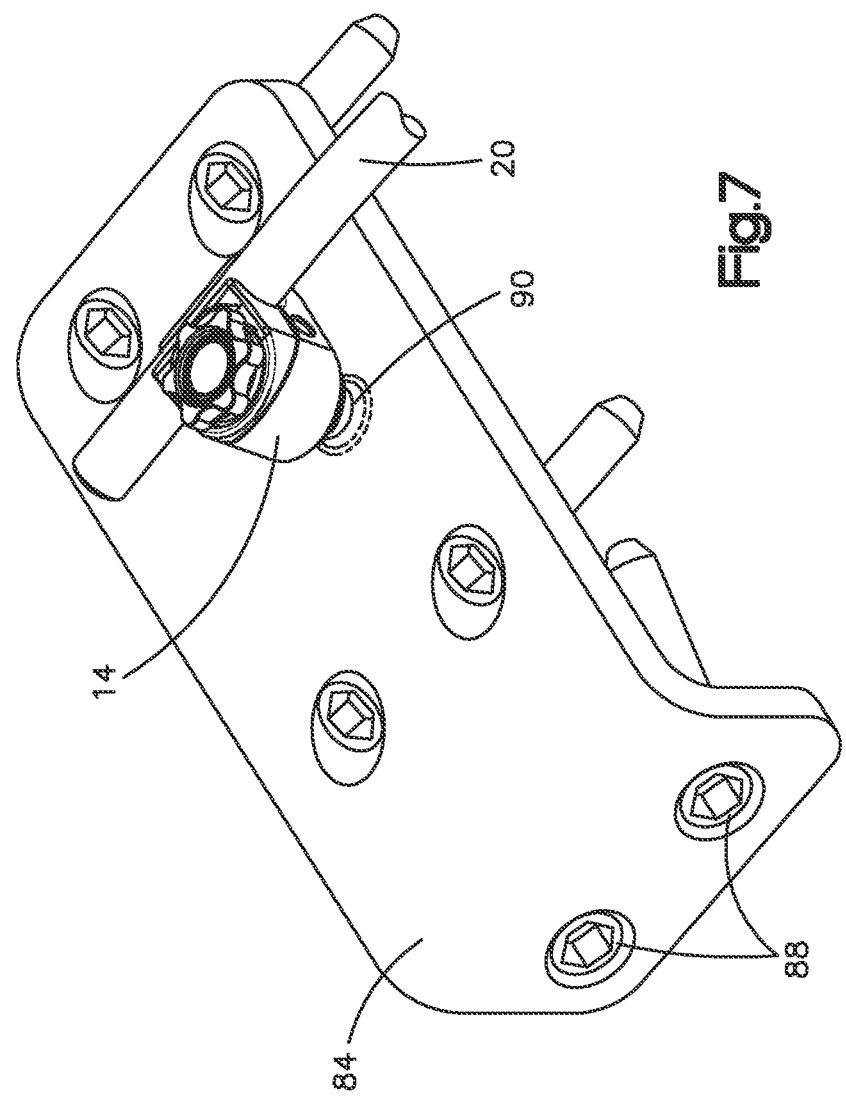
FIG. 7 is a perspective view of a plate and snap-fit fastener system.

FIG. 7 shows a plate configuration, wherein the pop-on, pop-off head including the clamp 14 and fastener 11 can be dropped onto a spherical head mounted on a plate 84 so as to secure part of one of the rods 20 along its pathway. The spherical head may also have a subjacent neck 90 to allow the same pivoting movement of the clamp 14 before final tightening. The plate 84 may define its own openings for receipt of fasteners 88, such as pedicle screws, to anchor it to the adjacent bone structures.

Figure 2C:
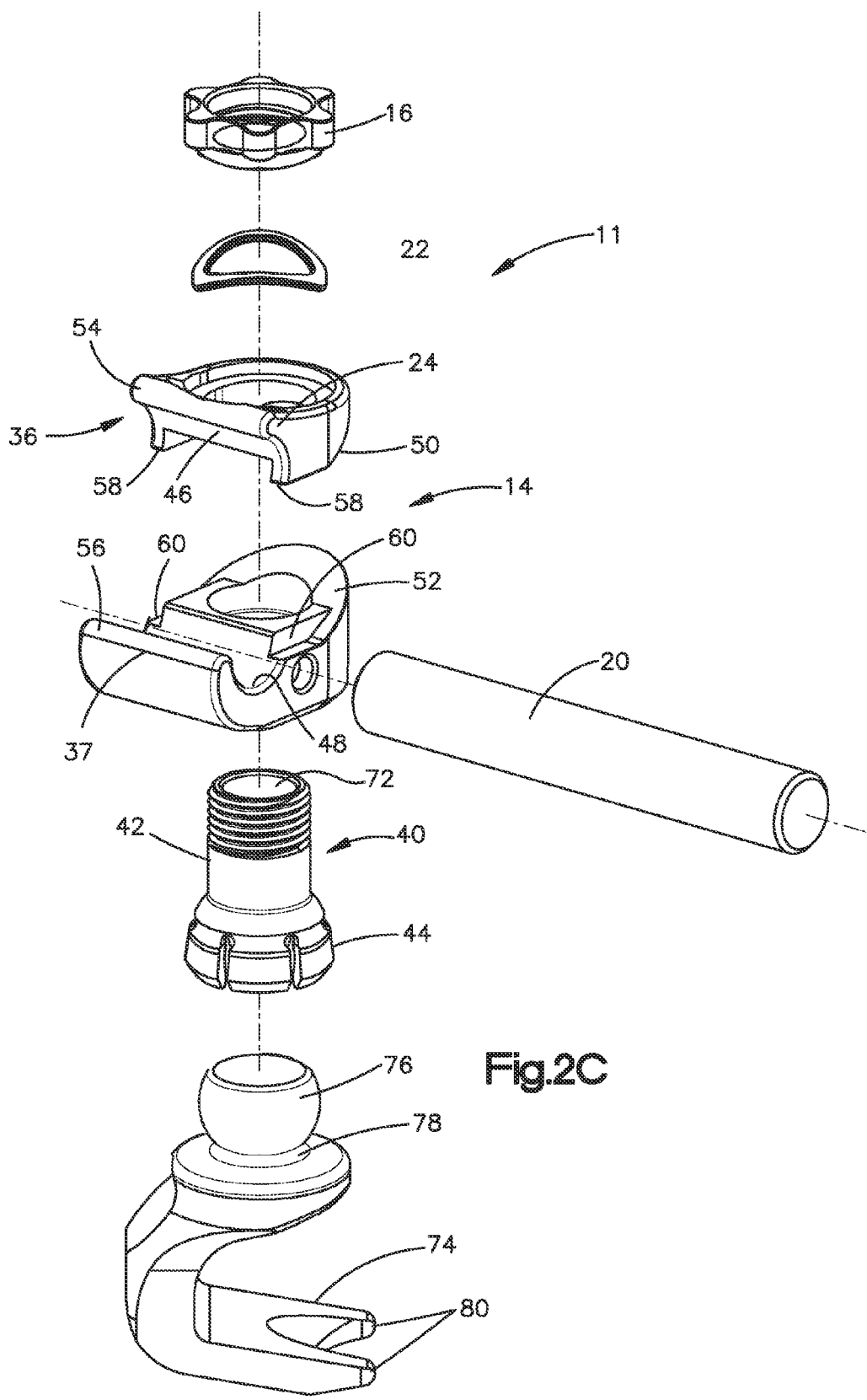
FIG. 2C is an exploded view of the fastener of FIG. 2A.

The system 10 may also include fasteners 11 including a hook 74 instead of a fixation shaft 12. The hook 74 includes a spherical head 76, a neck 78, a pair of prongs 80 and a fastener opening 82 as shown in FIGS. 2A-2C. The spherical head 76, similar to the pedicle screw described above, allows for poly-axial movement when connected via the collet 40 to the clamp 14. The neck 78 separates the spherical head from the body of the hook and provides some clearance for improved tilt, rotation and other poly-axial movement.

Extending from a free end of the hook is the pair of prongs 80 which have sharpened beveled edges configured to dig, bite or otherwise engage bony structures, such as on the spine. Once the prongs 80 are engaged, a separate fastener may be advanced through the bone and the fastener opening 82. Thus the hook 74 can support a snap-fit rod attachment similar to the fasteners 11. The clamp 14 operates in generally the same manner as with the attachment to a fastener 11 wherein securing of the connector 16 locks the collet 40 and jaws 36, 37 into place on the spherical head 76 and about the rod 20.

FIGS. 3A-3C show a mono-axial version of a hook 74 without a collet 40. Instead, the collet shaft 42 and skirt 44 are integrally connected or formed with the rest of the hook 74, as shown by the cross-section of FIG. 3B. This configuration allows for 360 degrees of rotation around the axis of the collet shaft 42 and a similar locking action of the clamp 14 onto the shaft and skirt 44. In another variation, the hook 74 up through the main jaw 37 could be combined into one component with a fixed orientation. Advantages over conventional hooks is the added rotational and poly-axial flexibility for the clamp 14, reducing the need to supply a wider range of fixed hooks and allowing improved flexibility for rod attachments.

Advantages of use of the clamp 14 with its poly-axial mounting and ability to reorient the clamp opening 18 offset from the axis of the pedicle screw 12 is that relatively low profile configurations (when compared to conventional pedicle screws) can be achieved. For example, height reductions of up to ⅓ may be achieved relative to a standard poly-axial pedicle screw. With a standard pedicle screw, the height of the rod mounted over the head of the screw is a fixed distance.

A number of aspects of the systems, devices and methods have been described. Nevertheless, it will be understood that various modifications may be made without departing from the spirit and scope of the disclosure. Accordingly, other aspects are within the scope of the following claims.

10 system
11 fasteners
12 fixation shaft
14 clamp
16 connector
18 clamp opening
20 rod
22 washer spring
24 pressure responsive portion
26 proximal end of fixation shaft
28 spherical head
30 neck
32 distal end
34 driver opening
36 upper jaw
37 main jaw
38 semi-spherical clamp opening
40 collet
42 collet shaft
44 collet skirt
46 arc member of 36
48 arc member of 37
50 sloped surface of 36
52 sloped surface
54 free end of 46
56 free end of 48
58 upper jaw flanges
60 lower jaw slots
62 cylindrical top portion of 70
64 semi-spherical bottom portion of 70
66 radial slots
68 central opening of connector
70 axial opening of clamp
72 axial opening of the collet
74 hook
76 spherical head
78 neck
80 prongs
82 fastener opening
84 plate
88 fasteners
90 neck That which is claimed:

1. A fastener for engaging a workpiece opening, the fastener comprising:
   a fixation shaft configured to frictionally engage the workpiece opening the fixation shaft including an at least partially spherical head at a proximal end; and
   a clamp including:
      an upper body and a main body that define an opening that extends in a direction perpendicular to a longitudinal axis of the clamp, wherein the opening does not intersect the longitudinal axis of the clamp, the upper body including a sloped surface and the main body including a complementary sloped surface, the sloped surfaces defining a pressure-responsive portion such that the sloped surface of the upper body moves along the sloped surface of the main body and modifies a size of the opening in response to pressure;
      an axial opening extending through the upper body and the main body along the longitudinal axis of the clamp for receiving at least a portion of a connector, the axial opening extending through at least a portion of the sloped surfaces of the upper and main bodies;
      a collet having a skirt defining a semi-spherical opening and a shaft extending from the skirt and configured to extend into the axial opening, the collet configured to compress the spherical head within the semi-spherical opening for locking engagement;

the connector being secured to the shaft of the collet to connect the clamp to the fixation shaft and exert pressure on the pressure-responsive portion of the clamp to modify the opening;

wherein the clamp is configured to pivotally engage a proximal end of the fixation shaft, and further wherein the clamp is offset from a longitudinal axis of the fixation shaft.

2. A fastener of claim 1, wherein the upper body includes an arc member and the main body includes an arc member and the arc members are configured to define the opening of the clamp.

3. A fastener of claim 2, wherein the opening of the clamp is a cylindrical opening.

4. A fastener of claim 3, wherein sloped surfaces result in both lateral and vertical movement of the upper body with respect to the main body upon exertion of pressure by the connector.

5. A fastener of claim 3, wherein the arc member of the upper body is shorter than the arc member of the main body so as to define an upwardly directed slot accessing the opening of the clamp.

6. A fastener of claim 3, wherein the arc member of the main body is shorter than the arc member of the main body so as to define a downwardly directed slot accessing the opening of the clamp.

7. A fastener of claim 4, wherein the lateral movement shortens a distance between free ends of the arc members.

8. A fastener of claim 7, further comprising a spring extending between the upper body and the connector.

9. A fastener of claim 8, wherein the spring is configured to assume a fully deformed condition upon tightening of the connector.

10. A fastener of claim 8, wherein the spring is deformed by external pressure urging the free ends of the arc members apart.

11. A fastener of claim 10, wherein the free ends of the arc members define cam surfaces.

12. A fastener of claim 1, wherein the connector is configured to connect to the shaft of the collet to compress the body of the clamp therebetween.

13. A fastener of claim 12, wherein compression of the body deforms the skirt to lock onto the spherical head.

14. A fastener of claim 13, wherein the connector includes a threaded nut configured to engage a plurality of threads on the shaft of the collet.

15. A fastener of claim 14, wherein the shaft of the collet defines an axial opening and the threaded nut defines an axial opening configured to align with the axial opening of the shaft when engaged thereto.

16. A fastener of claim 14, wherein the skirt is configured to allow at least plus or minus degrees of tilt of the clamp with respect to a plane orthogonal to an axis of the fixation shaft.

17. A fastener of claim 15, wherein the skirt defines at least one radial relief cut configured to facilitate deformation of the skirt about the spherical head.

18. A fastener of claim 17, further comprising a spring washer configured for placement between the threaded nut and the body of the clamp.

19. A fastener of claim 1, wherein the pressure-responsive portion is configured to decrease the size of the opening in response to pressure applied thereto.

20. A fastener of claim 19, wherein the clamp is configured for locking engagement with the proximal end of the fixation shaft in response to pressure applied by the connector.

21. A fastener of claim 1, wherein relative movement of the upper body and main body is locked upon tightening of the connector.

* * * * *